(12) United States Patent
Lim

(10) Patent No.: US 7,462,182 B2
(45) Date of Patent: Dec. 9, 2008

(54) REDUCING INSTRUMENT FOR SPINAL SURGERY

(75) Inventor: Roy Lim, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 479 days.

(21) Appl. No.: 10/915,005

(22) Filed: Aug. 10, 2004

(65) Prior Publication Data

US 2006/0036254 A1     Feb. 16, 2006

(51) Int. Cl.
*A61B 17/58* (2006.01)
(52) U.S. Cl. .................................................. 606/99
(58) Field of Classification Search ............... 606/61, 606/86, 90, 99, 104, 279
See application file for complete search history.

(56) References Cited

U.S. PATENT DOCUMENTS

| | | | |
|---|---|---|---|
| 3,604,487 A | 9/1971 | Gilbert | |
| 3,844,291 A | 10/1974 | Moen | |
| 4,411,259 A | 10/1983 | Drummond | |
| 4,911,154 A * | 3/1990 | Vickers | 606/104 |
| 5,020,519 A | 6/1991 | Hayes et al. | |
| 5,113,685 A | 5/1992 | Asher et al. | |
| 5,314,431 A | 5/1994 | Graziano | |
| 5,330,472 A | 7/1994 | Metz-Stavenhagen | |
| 5,364,397 A | 11/1994 | Hayes et al. | |
| 5,389,099 A | 2/1995 | Hartmeister et al. | |
| 5,449,361 A | 9/1995 | Preissman | |
| 5,458,608 A | 10/1995 | Wortrich | |
| 5,466,243 A | 11/1995 | Schmieding et al. | |
| 5,616,143 A | 4/1997 | Schlapfer et al. | |
| 5,720,751 A | 2/1998 | Jackson | |
| 5,782,830 A | 7/1998 | Farris | |
| 5,899,901 A | 5/1999 | Middleton | |
| 5,910,141 A | 6/1999 | Morrison et al. | |
| 5,944,720 A | 8/1999 | Lipton | |
| 6,036,692 A | 3/2000 | Burel et al. | |
| 6,042,582 A | 3/2000 | Ray | |
| 6,063,088 A | 5/2000 | Winslow | |
| 6,440,133 B1 * | 8/2002 | Beale et al. | 606/61 |
| 6,648,888 B1 | 11/2003 | Shluzas | |
| 6,660,006 B2 * | 12/2003 | Markworth et al. | 606/61 |

(Continued)

FOREIGN PATENT DOCUMENTS

DE      42 38 339 A1      5/1994

OTHER PUBLICATIONS

U.S. Appl. No. 10/789,610, filed Feb. 27, 2004, Lim.

*Primary Examiner*—Eduardo C Robert
*Assistant Examiner*—Michael J Araj
(74) *Attorney, Agent, or Firm*—Krieg DeVault LLP

(57) ABSTRACT

An instrument is provided for use in orthopedic surgery for reduction of a connecting member such as a spinal rod toward an anchor. The reducing instrument includes an actuating assembly, a shaft assembly extending distally from the actuating assembly, and a distal engaging assembly. The distal engaging assembly includes a pair of arms movable toward and away from one another in response to proximal and distal movement of a reducing member of the shaft assembly. The arms are pivotally engageable to the anchor to facilitate alignment of the shaft assembly with the anchor. With the connecting member extending between the arms and also between the reducing member and the anchor, distal movement of the reducing member with the actuating assembly seats the connecting member in the anchor.

54 Claims, 7 Drawing Sheets

U.S. PATENT DOCUMENTS

| | | | |
|---|---|---|---|
| 6,790,208 B2 * | 9/2004 | Oribe et al. | 606/53 |
| 2003/0028195 A1 | 2/2003 | Bette | |
| 2003/0225408 A1 * | 12/2003 | Nichols et al. | 606/61 |
| 2004/0049191 A1 | 3/2004 | Markworth et al. | |
| 2005/0090824 A1 * | 4/2005 | Shluzas et al. | 606/61 |
| 2005/0131420 A1 * | 6/2005 | Techiera et al. | 606/99 |

* cited by examiner

REDUCING INSTRUMENT FOR SPINAL SURGERY

BACKGROUND

In orthopedic surgical procedures, it is known to implant devices to support bones or other tissue, to correct deformities, to hold tissues in position for healing after injuries or other surgery, and for other purposes relating to orthopedic health. For example, where correction of a scoliotic or other abnormal curvature or misalignment of the spine is desired, a sturdy rod, plate, or other elongated connecting member can be placed along one or more vertebral segments to support or hold the segments in a corrected position. Bone screws, bone hooks or other fixation implants are attached to vertebrae and connected to the connecting member to secure the connecting member along the spinal column.

Commonly, the fixation implants and the connecting member(s) are placed separately, that is, they are not connected together prior to implantation in the body. For example, bone screws may be implanted into vertebrae first, connectors may be placed on or around the screws (if necessary), and then the connecting member may be placed into the body. The connecting member may be contoured prior to insertion to approximate the curvature desired, or it may be contoured after placement adjacent the spine. In cases where a connecting member and bone screws or other fixation elements are separately placed, the connecting member and screws may be required to be forced toward each other for connection. The process of moving the connecting member and fixation elements toward each other for connection is generally termed "reduction."

Reduction can be accomplished by hand, although the environment and close quarters of a surgical site can make reduction by hand quite difficult. While instruments have been developed to provide a mechanical advantage in reducing or positioning the connecting member relative to an anchor, there remains a need for reducing instruments which are maneuverable relative to the anchor and connecting member to facilitate insertion and manipulation of the connecting member and anchor through the incision or portal in which the reducing instrument is positioned.

SUMMARY

The present invention concerns tools for use in implanting orthopedic implants during surgery. Specifically, the present invention is directed to tools for reduction of a connecting member.

According to one aspect, an instrument for reducing a connecting member relative to an anchor includes an actuating assembly and a shaft assembly. The shaft assembly extends distally from the actuating assembly and includes a reducing member extending through an outer sleeve. The reducing member is movable distally and proximally relative to the outer sleeve with the actuating assembly. The instrument further includes an engaging assembly at a distal end of the shaft assembly having a pair of arms movable between an open position for receiving the anchor and connecting member therebetween and an engaged position for engaging opposing sides of the anchor. In the engage position, the instrument can be pivoted about the anchor with the connecting member between the arms. The reducing member includes a distally opening receptacle for receiving the anchor and to align the anchor with the shaft assembly as the reducing member is moved distally toward the anchor to move the connecting member and anchor relative to one another.

In another aspect, an instrument for reducing a connecting member relative to an anchor, includes an actuating assembly and a shaft assembly extending distally from the actuating assembly. The shaft assembly includes a reducing member extending through an outer sleeve that is movable distally and proximally relative to the outer sleeve with the actuating assembly. The instrument includes an engaging assembly at a distal end of the shaft assembly that includes a pair of arms pivotally coupled to the outer sleeve. The arms are movable upon distal advancement of the reducing member relative to the outer sleeve between an open position for receiving the anchor and connecting member therebetween to an engaged position wherein the arms engage opposing sides of the anchor.

In another aspect, an instrument for reducing a connecting member relative to an anchor includes an actuating assembly and a shaft assembly extending distally from the actuating assembly. The shaft assembly includes a reducing member extending through an outer sleeve that is movable distally and proximally relative to the outer sleeve with the actuating assembly. The instrument includes an engaging assembly at a distal end of the shaft assembly that includes a pair of arms pivotally mounted to the shaft assembly and movable between an open position for receiving the anchor and connecting member therebetween and an engaged position for engaging the anchor therebetween. The reducing member engages the pair of arms in the engaged position to maintain the pair arms in the engaged position.

These and other aspects will also be apparent from the following description.

DESCRIPTION OF THE ILLUSTRATED EMBODIMENT

Figure 1:
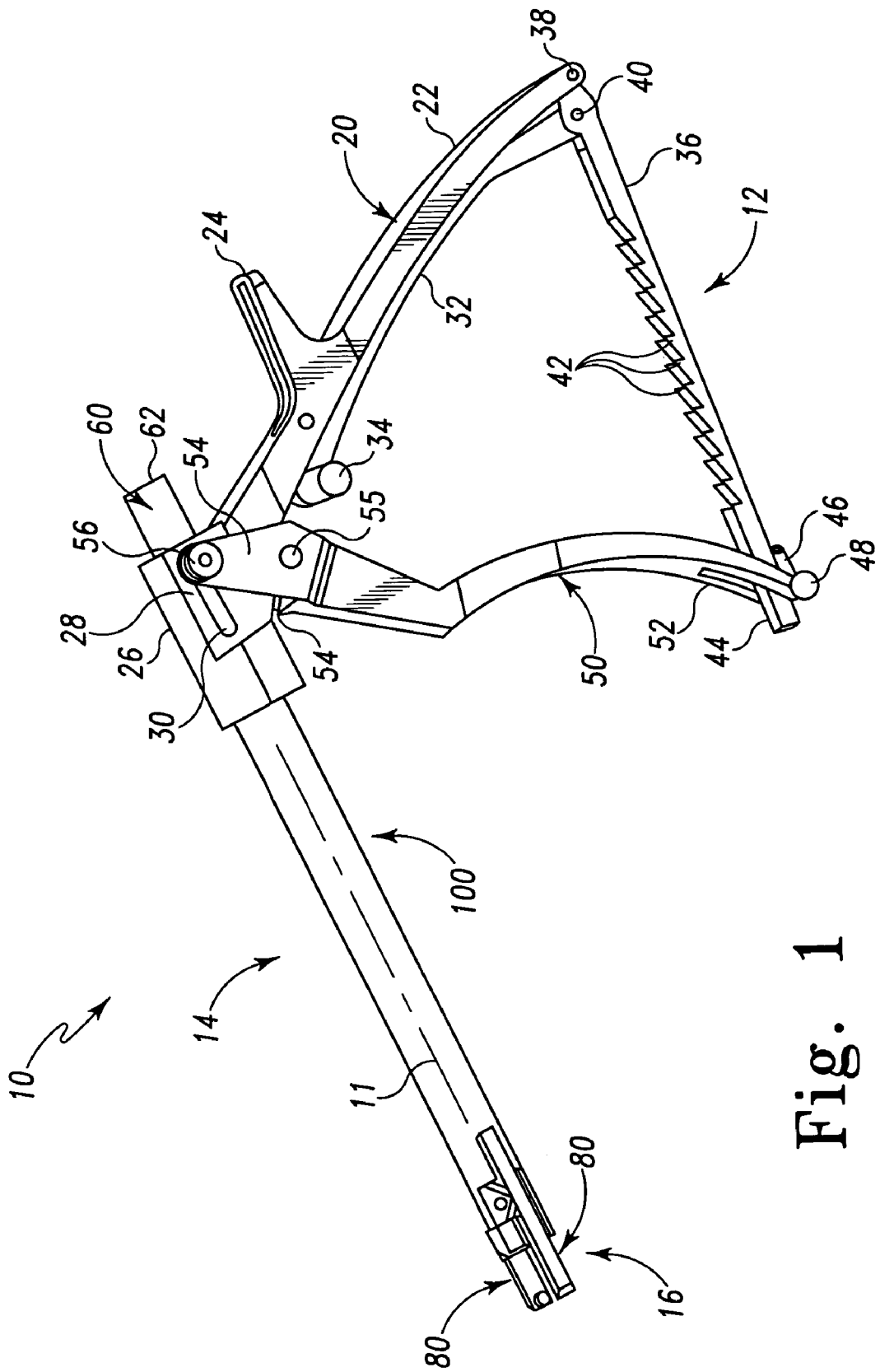
FIG. 1 is a perspective view of a reducing instrument.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein are contemplated as would normally occur to one skilled in the art to which the invention relates.

Referring to FIG. 1 there is shown a reducing instrument 10 removably engageable to an anchor and operable to move a rod or other elongated connecting member and the anchor toward another. Reducing instrument 10 includes an actuating assembly 12, a shaft assembly 14 extending distally from actuating assembly 12, and an anchor engaging assembly 16 at a distal end of shaft assembly 14. Engaging assembly 16 is pivotally engageable to the anchor to allow reducing instrument 10 to be pivoted relative to the anchor to position reducing member shaft assembly 14 in alignment with the anchor. Engagement of reducing instrument 10 to the anchor is facilitated since the reducing instrument need not be aligned in any particular orientation for engagement with the anchor, allowing good visibility of the anchor and remote positioning of the reducing instrument in alignment with the anchor. This pivotal coupling arrangement allows reducing instrument 10 to be coupled to an anchor in any one of a number of approaches to the anchor that may necessitated by visual considerations, anatomical considerations, or the size and location of the access portal to the anchor. Reducing instrument 10 can thereafter be pivoted to an aligned position with the anchor to position or reduce the connecting member into the anchor and facilitate engagement of the connecting member to the anchor.

Engaging assembly 16 and shaft assembly 14 are remotely operable with actuating assembly 12 to selectively engage and release the anchor and to distally advance the reducing member. Actuating assembly 12 includes a first handle 20 and a second handle 50 extending from the proximal end of shaft assembly 14. Handles 20, 50 are transversely oriented to shaft assembly 14 and laterally offset therefrom to facilitate viewing of the distal end of shaft assembly 14 and engaging assembly 16.

First handle 20 includes a gripping portion 22 with a free end, an intermediate proximal extension 24, and a housing 26 extending from handle 20 opposite its free end. Shaft assembly 14 extends distally from housing 26, and includes an outer sleeve 100 fixed to housing 26 and extending distally therefrom. Shaft assembly 14 further includes a reducing member 60 extending through and movable relative to housing 26 and outer sleeve 100 with actuating assembly 12. Reducing member 60 includes a proximal end 62 projecting proximally of housing 26.

Housing 26 includes a connection region 28 between handle 20 and housing 26. Connection region 28 includes a flat surface profile and a slot 30 extending therethrough in communication with reducing member 60. The opposite side of housing 26 (not shown) can be similarly provided with a flat surface profile and slot extending therethrough. Second handle 50 includes coupling arms 54 extending along opposite sides of housing 26 and along connection region 28. A pivot pin 55 pivotally couples second handle 50 to first handle 20. Slot 30 receives a coupling pin 56 therethrough to pivotally couple second handle 50 to reducing member 60. Coupling arms 54 are rotatable relative to coupling pin 56 about pivot pin 55, and second handle 50 is movable toward first handle 20 to advance coupling pin 56 and thus reducing member 60 distally in slot 30. This movement of second handle 50 distally advances reducing member 60 relative to outer sleeve 100.

Figure 12:
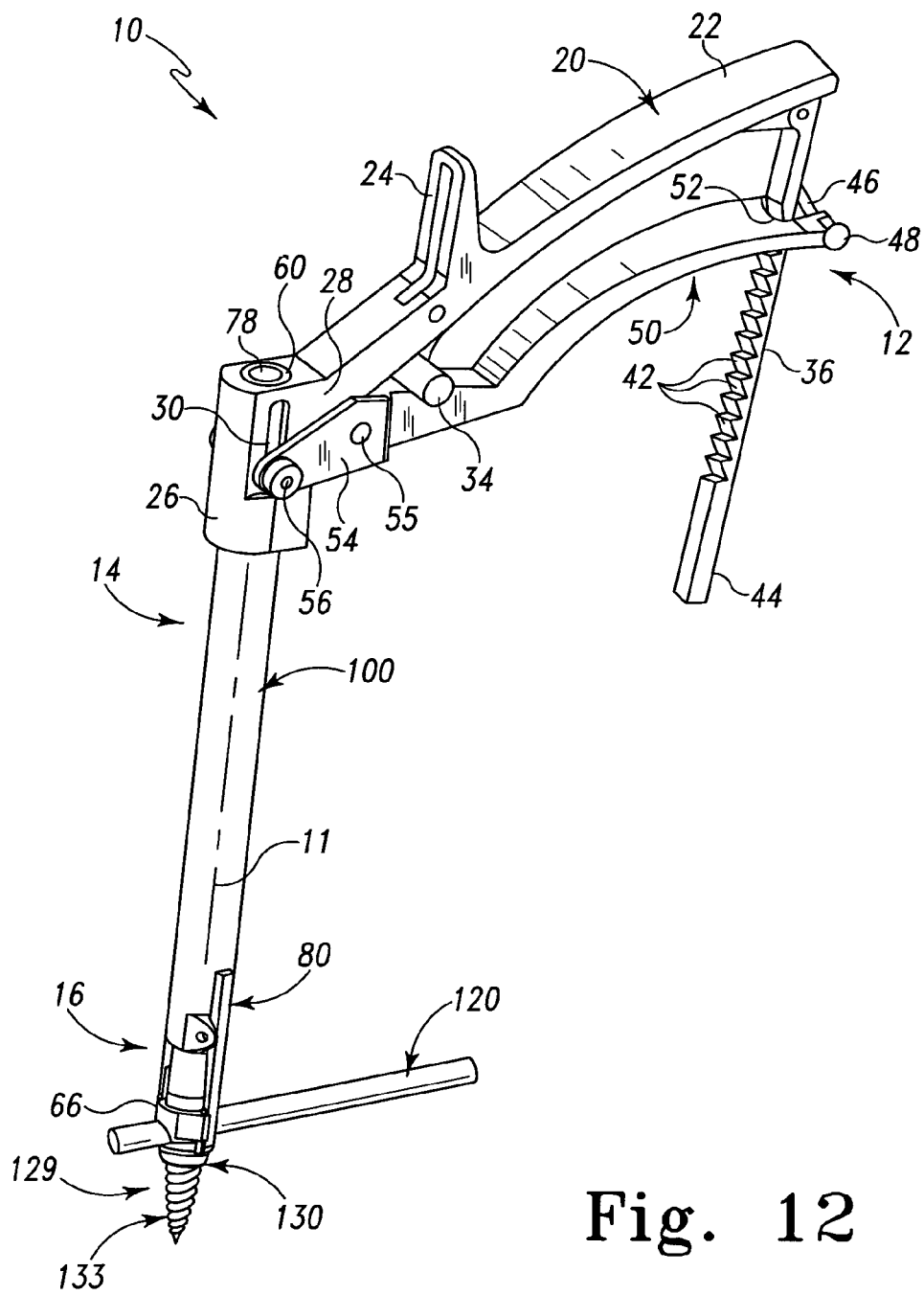
FIG. 12 is a perspective view of the reducing instrument engaged to the anchor and manipulated to seat the connecting member in the anchor.

Adjacent its free end first handle 20 includes a first connection pin 38 that pivotally couples a locking arm 36 to first handle 20. Locking arm 36 extends from first handle 20 to an opposite free end 44, where it extends through a slot 52 in second handle 50. Locking arm 36 includes a number of teeth 42 therealong oriented toward an upper end of slot 52. A spring housing 48 houses a spring coupled to a biasing member 46 to bias biasing member 46 toward and into engagement with locking arm 36. Biasing member 46 maintains locking arm 36 in a biased position toward the upper end of slot 52. As second handle 50 is pivoted toward first handle 20, second handle 50 moves along locking arm 36, as shown in FIG. 12. The upper end of slot 52 engages an adjacent one of teeth 42 to maintain a position of second handle 50 relative to first handle 20. This in turn maintains the distal displacement of reducing member 60 relative to outer sleeve 100 and engaging assembly 16.

Actuating assembly 12 further includes a release arm 32 fixedly coupled via a second connection pin 40 to locking arm 36 adjacent first connection pin 38. Release arm 32 extends adjacent first handle 20 along a side thereof oriented toward second handle 50. Release arm 32 further includes an extension member 34 opposite second connection pin 40 which extends laterally from the space between handles 20, 50. Extension member 34 can be readily engaged with the thumb of the user and pushed away from first handle 20 by pushing extension member 34 toward second handle 50. This in turn rotates locking arm 36 and release arm 32 about first connection pin 38, thereby pushing locking arm 36 against the bias of biasing member 46 and away from the upper end of slot 52. This releases the upper end of slot 52 from its engagement with teeth 42, allowing second handle 50 to be pivoted away from first handle 20 about pin 55 from its position in FIG. 12 toward its position shown in FIG. 1.

Figure 2:
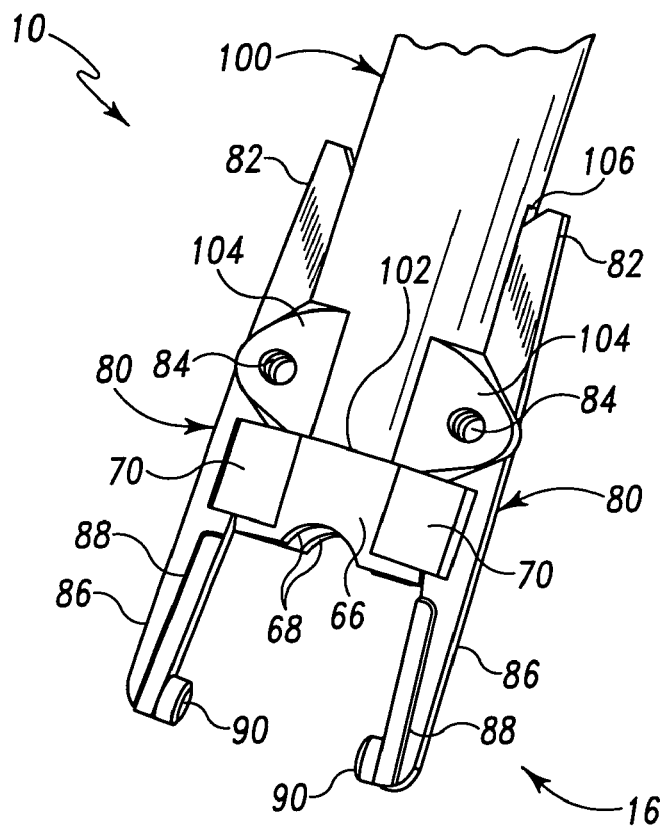
FIG. 2 is a perspective of a distal portion of the reducing instrument shown in FIG. 1 in an open position.
Figure 3:
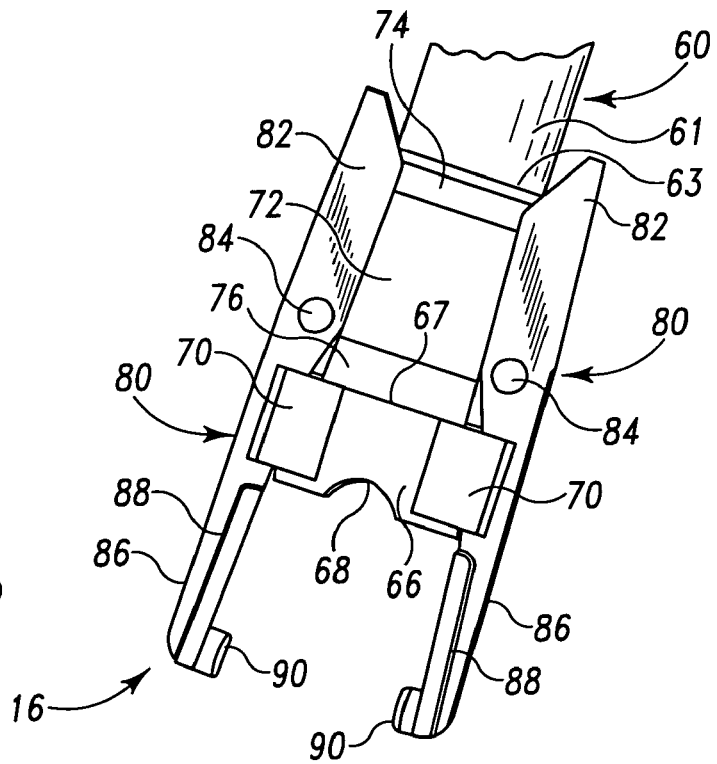
FIG. 3 is the view of the distal portion of the reducing instrument of FIG. 2 with an outer sleeve member removed and the clamping arms in an open position.

In FIGS. 2 and 3, there is shown engaging assembly 16 and reducing member 60 at the distal portion of reducing instrument 10. In FIG. 3, outer sleeve 100 is removed to show the distal portion of reducing member 60 and its contact with engaging assembly 16 in the open position. Reducing member 60 includes a bore 78 (FIG. 12) extending therethrough and opening at proximal end 62 and also opening at a distal end member 66 of reducing member 60. End member 66 is enlarged relative to the proximal portion of reducing member 60, forming a proximally facing lip 67. Reducing member 60 includes opposite ears 70 extending laterally from end member 66. Outer sleeve 100 includes a distal end 102 positionable in contact with proximally facing lip 67 of end member 66 when engaging assembly 16 is an open position, as shown in FIG. 2. Outer sleeve 100 includes opposite wings 104 extending laterally therefrom that are spaced proximally of and aligned with ears 70.

Engaging assembly 16 includes a pair of arms 80 pivotally coupled to respective ones of the wings 104 with a pivot pin 84. Arms 80 each include a proximal portion 82 extending proximally from pivot pin 84, and a distal portion 86 extending distally from pivot pin 84. Each of the arms 80 includes an inwardly facing lug 90 adjacent a distal end of the respective arm 80. Lugs 90 have a circular cross-section, and a cylindrical shape extending from the respective arm 80. Lugs 90 are positionable in a respective one of opposite detents of the anchor to pivotally engage reducing instrument 10 to the anchor, as discussed further below. Each arm 80 further includes a rail 88 extending therealong from the distal end of the arm 80 to a location spaced distally of the distal end of ears 70 when in the open position shown in FIGS. 2 and 3.

Reducing member 60 includes a proximal cylindrical sleeve portion 61 and a tapered portion 72. Tapered portion 72 is frusto-conical and proximally tapered to proximal transition portion 74. Proximal transition portion 74 is tapered distally and extends between the proximal end of tapered portion 72 and the distal end 63 of proximal sleeve portion 61. A distal transition portion 76 extends between the distal end of tapered portion 72 and end member 66. Distal transition portion 76 is cylindrical in size and shape and approximates the same size and shape as proximal sleeve portion 61.

As shown in FIG. 2, outer sleeve 100 includes slots 106 (only one shown) extending along the distal end thereof in communication with tapered portion 72 and proximal transition portion 74. Slots 106 allow proximal portions 82 of arms 80 to contact tapered portion 72 and proximal transition portion 74 through outer sleeve 100 without interference from outer sleeve 100. In the open position of engaging assembly 16, arms 80 can be biased with a spring (not shown) in ears 104 to extend along tapered portion 72 as shown in FIG. 3 so that proximal portions 82 are positioned in contact with tapered portion 72. The proximal portions 82 of arms 80 are contoured to lie along proximal transition portion 74, allowing lugs 90 at the distal ends of arms 80 to be separated from one another a sufficient distance to allow placement of the anchor therebetween. Ears 70 are spaced proximally from rails 88 to allow arms 80 to freely pivot about pins 84 to the open position. In the open position, the distal end of sleeve 100 is positioned about distal transition portion 76 in engagement with lip 67 to limit proximal movement of reducing member 60 relative to outer sleeve 100.

Figure 4:
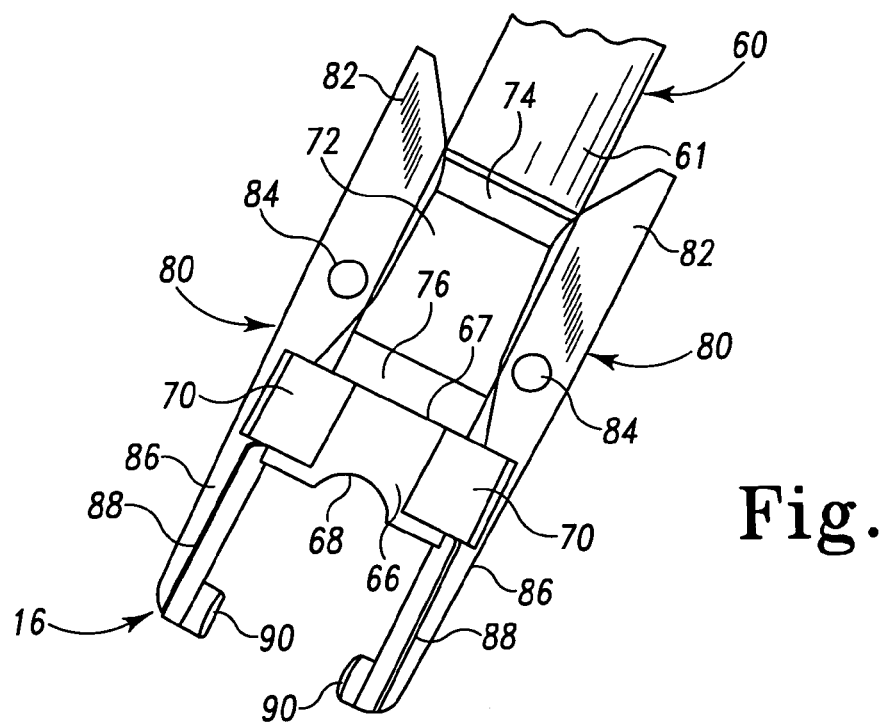
FIG. 4 is the view of the distal portion of the reducing instrument of FIG. 3 with the clamping arms in an engaged position.
Figure 5:
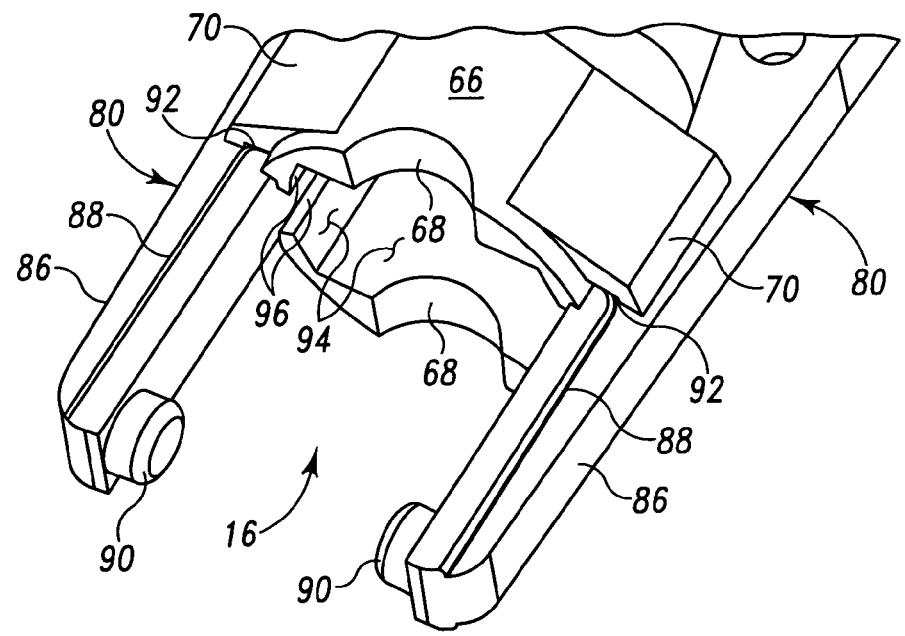
FIG. 5 is another perspective view of the distal portion of the reducing instrument of FIG. 4.

FIGS. 4 and 5 show reducing member 60 advanced distally relative to arms 80 with actuating assembly 12. Outer sleeve 100 is not shown for clarity. Distal advancement of reducing member 60 moves ears 70 distally along arms 80 until rails 88 are received in respective ones of the recesses 92 of ears 70. Simultaneously, the contoured surface of proximal portions 82 of arms 80 ride along proximal transition portion 74 and into contact with proximal sleeve portion 61. The larger diameter proximal sleeve portion 61 pushes the proximal ends 82 away from one another against the bias of arms 80, and moving the distal ends of arms 80 toward one another about pins 84 to the engaged position. As ears 70 move further distally along rails 88, rails 88 remain engaged by ears 70 to maintain arms 80 in the engaged position relative to one another. A space 96 extends along each side of end member 66 and receives the adjacent rail 88 as end member 66 is moved therealong. End member 66 contacts arms 80 along the space 96 in the engaged position to limit movement of the arms 80 toward one another. Accordingly, ears 70 and end member 66 capture arms 80 therebetween as the reducing member is distally advanced along arms 80.

Figure 6:
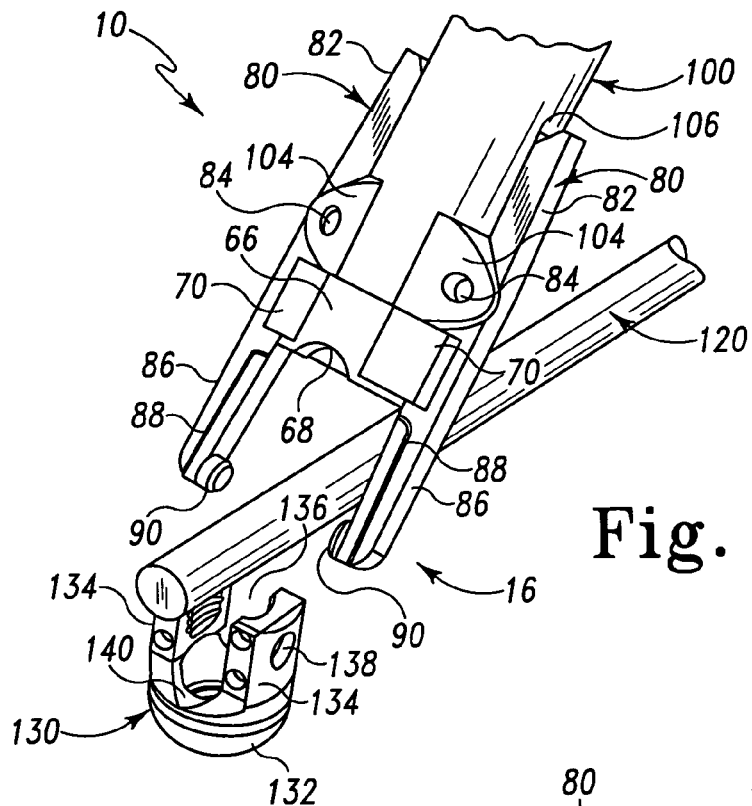
FIG. 6 is a perspective view showing the distal portion of the reducing instrument with its clamping arms in an open position and being directed toward a connecting member and anchor.

The operation of reducing instrument 10 to engage an anchor and seat a connecting member in the anchor will be described with reference to FIG. 1 and FIGS. 6-12. Reducing instrument 10 is manipulated so that engaging assembly 16 is in an open position, as shown in FIGS. 1 and 6. An anchor 129 including a receiver member 130 is engaged to the spinal column, and receiver member 130 is configured to receive and engage an elongate connecting member along the spinal column. As shown in FIG. 6, receiver member 130 includes a cup portion 132 and a pair of arms 134 extending from opposite sides of cup portion 132 and generally parallel to an alignment axis 131. Arms 134 form a passage 136 therebetween for receiving connecting member 120 therein in a direction transversely oriented to alignment axis 131. Arms 134 can also be internally or externally threaded to receive a set screw or nut to engage the connecting member 120 in passage 136. Alignment axis 131 can be aligned with such threading such that when the set screw, nut or other securing member is advanced along axis 131 it properly engages arms 134 without, for example, cross-threading or other misalignment.

Cup portion 132 includes a lower opening through which a bone engaging portion 133 of the anchor 129 extends for engaging a bony portion of the spinal column. The head of the bone engaging portion 133 is seated in cup portion 132 below passage 136. The head portion can be pivotally received in cup portion 132 to allow receiver member 130 to assume any one of a plurality of positions relative to bone engaging portion 133 at least prior to engagement of connecting member 120 in passage 136. The bone engaging portion 133 can be a bone screw with an enlarged head in cup portion 132 and a threaded shaft extending through the lower opening of receiver member 130. Other embodiments contemplate other forms for the anchor, including a hook type bone engaging portion and mono-axial arrangements between the receiver member and the bone engaging portion.

After engagement of the anchor 129 to the bony portion, connecting member 120 is positioned adjacent receiver member 130. It is contemplated that a number of anchors 129 can be positioned and engaged along the spinal column, and connecting member 120 can be engaged in the receiver member of one of the anchors. Due to misalignment of the vertebrae, misalignment of the receiver members of the anchors, or other conditions, connecting member 120 cannot be easily or readily positioned seated in receiver member 130. For example, it may be desired to seat connecting member 120 against a seat 140 in receiver member 130, against the head of the bone engaging portion, or against a cap or other device between the bone engaging portion and the connecting member.

Figure 7:
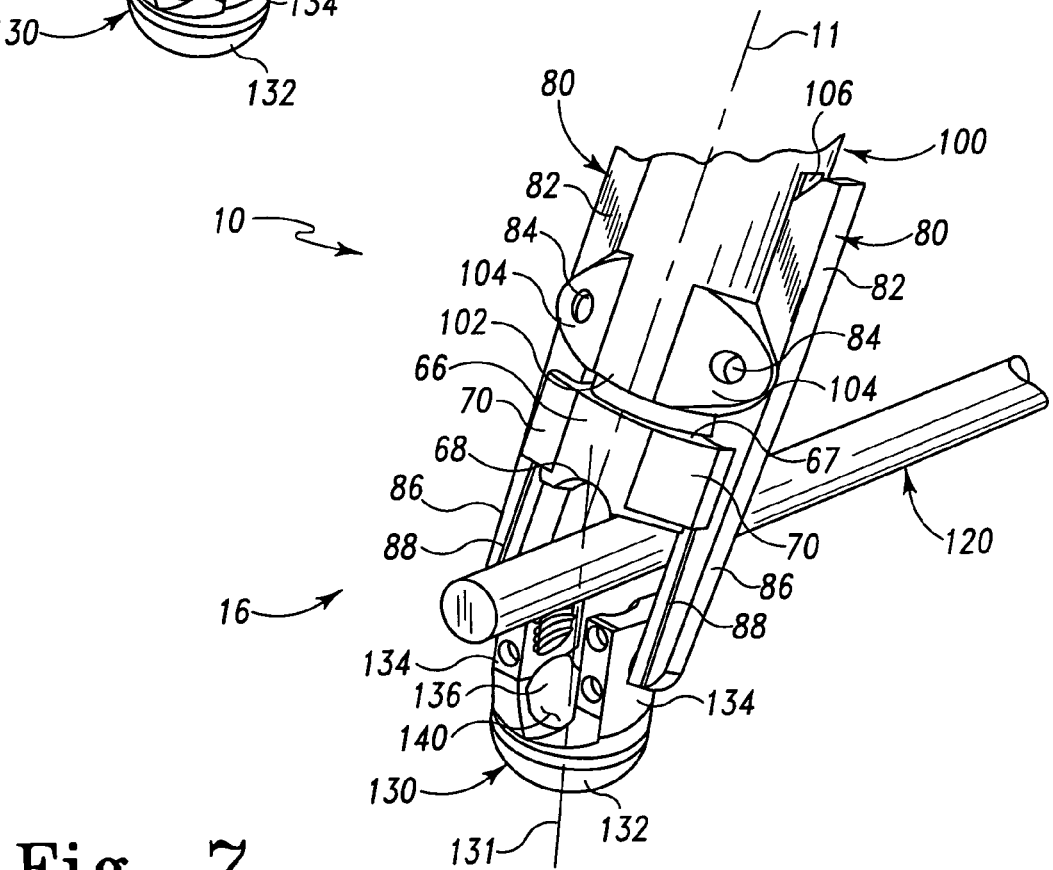
FIG. 7 is a perspective view showing the distal portion of the reducing instrument positioned over the connecting member and prior to engagement of the clamping arms to the anchor.

In FIG. 7 arms 80 of engaging assembly 16 are positioned along the outside of arms 134 of receiver member 130 with connecting member 120 between arms 80 and between end member 66 and receiver member 130. Reducing member 60 is moved distally with actuating assembly 12 so that ears 70 are moved toward and engage rails 88, which in turn moves lugs 90 of arms 80 toward one another to engage detents 138 in arms 134 of receiver member 130. Lugs 90 are rotatably received in respective ones of the circular detents 138 of arms 134, allowing reducing instrument 10 to pivot about receiver member 130 even when engaged thereto with lugs 90. Accordingly, reducing instrument 10 can be engaged to receiver member 130 from any one of a number of approaches to receiver member 130, even when the longitudinal axis 11 of reducing instrument 10 is not aligned with alignment axis 131, as shown in FIG. 7.

Figure 8:
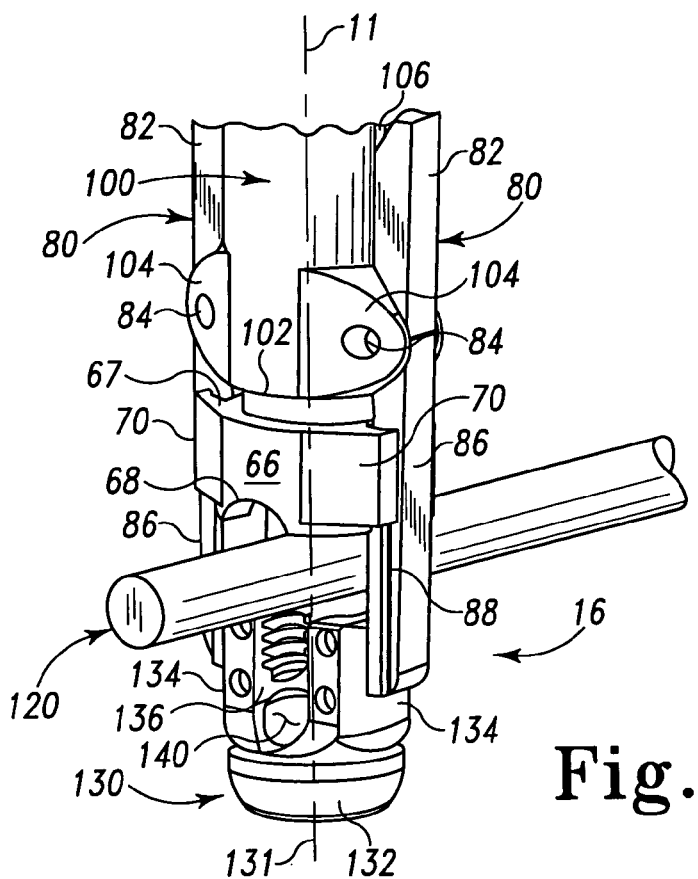
FIG. 8 is a perspective view of the distal portion of the reducing instrument engaged to the anchor and with the connecting member between the clamping arms.
Figure 9:
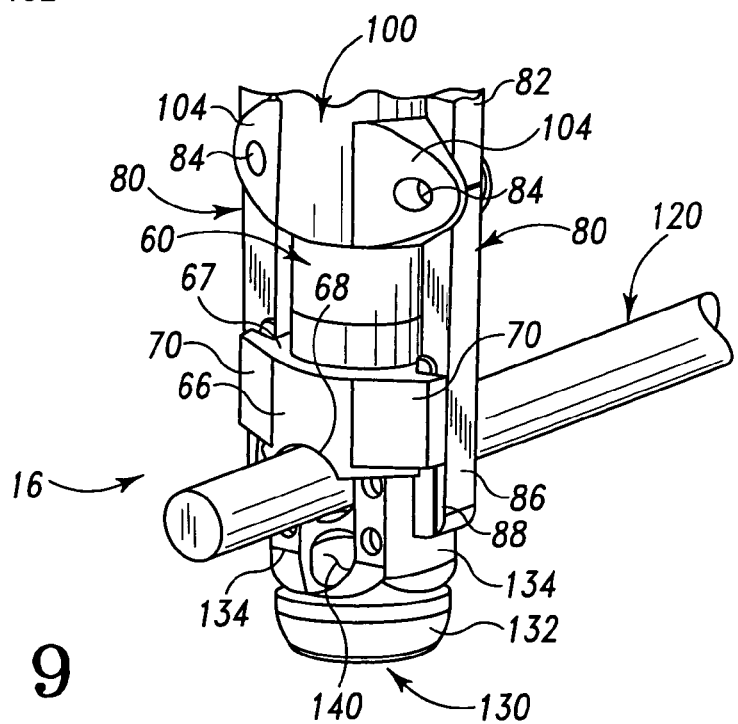
FIG. 9 is a perspective view of the distal portion of the reducing instrument being moved to reduce the connecting member and anchor relative to one another.

Reducing instrument 10 can be pivoted about receiver member 130 to align longitudinal axis 11 of reducing instrument 10 with axis 131 extending between arms 134, as shown in FIG. 8. When aligned, reducing member 60 is further advanced distally relative to outer sleeve 100 and into contact with connecting member 120, as shown in FIG. 9. Ears 70 move distally along rails 88 until end member 66 contacts connecting member 120. End member 66 includes a distally oriented recess 68 that receives connecting member 120 to maintain connecting member 120 in contact and alignment with end member 66 as it is moved toward receiver member 130. Recess 68 is formed by a concavely curved surface that provides form-fitting engagement with the outer surface of connecting member 120.

Figure 10:
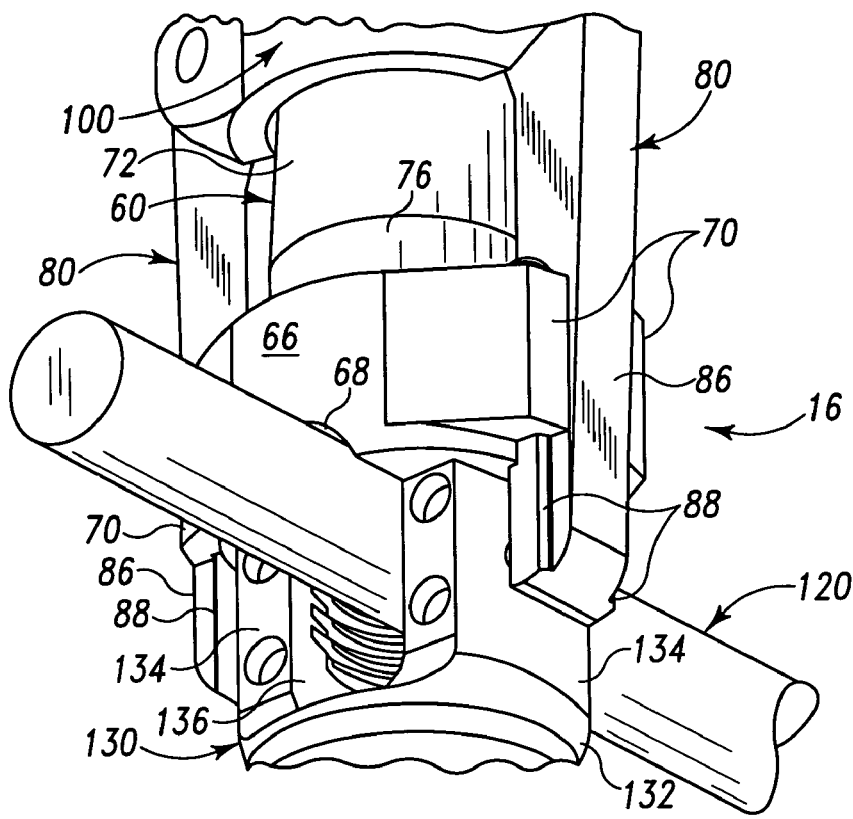
FIG. 10 is another perspective view of the distal portion of the reducing instrument being moved to reduce the connecting member and anchor relative to one another.

As shown in FIGS. 5 and 10, reducing member 60 includes a distally opening receptacle 94 in end member 66 sized and shaped to non-rotatably receive arms 134 of receiver member 130. Receptacle 94 provides a close fit with arms 134 to align receiver member 130 with bore 78 extending through reducing member 60. As shown in FIGS. 9 and 10, as reducing member 60 is advanced distally, receiver member 130 is received into receptacle 94 to maintain an aligned position of receiver member 130 within reducing member 60. Also, recess 68 of end member 66 is aligned with passage 136 of receiver member 130. Connecting member 120 is seated within recess 68, which maintains connecting member 120 in alignment with passage 136 as it is seated into receiver member 130.

Figure 11:
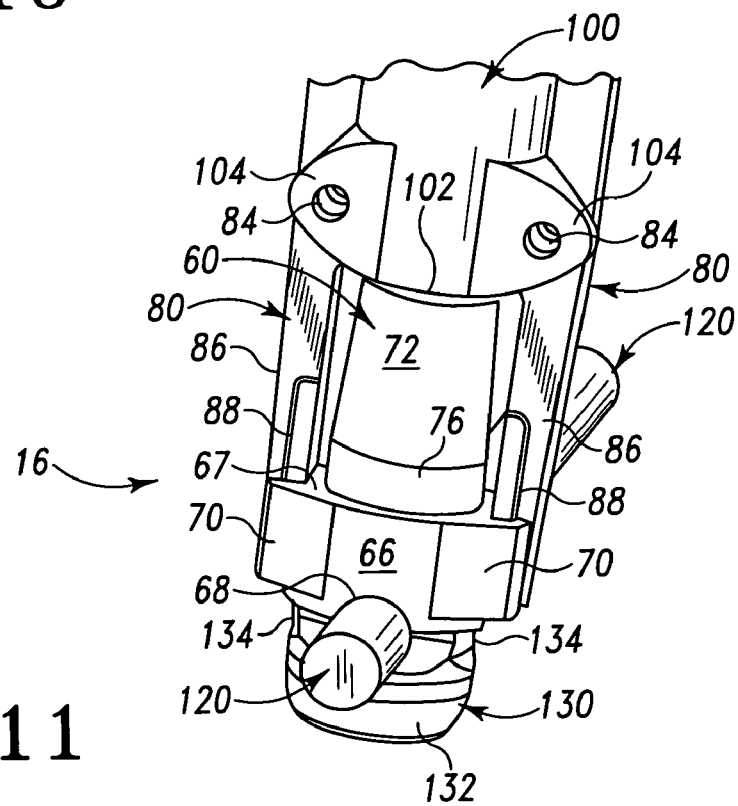
FIG. 11 is a perspective view of the distal portion of the reducing instrument moved to seat the connecting member in the anchor.

In FIG. 11 reducing member 60 is advanced further distally about arms 134 to displace connecting member 120 distally between arms 134 for seating in receiver member 130. Actuating assembly 12 includes locking arm 36 to maintain the distal placement of reducing member 60 and thus maintain connecting member 120 seated in receiver member 130. A set screw, nut or other securing device is delivered through bore 78 and engaged to arms 134 to secure connecting member 120 in receiver member 130. The positioning of arms 134 in receptacle 94 of reducing member 60 ensures that the securing device does not become misaligned with the arms 134 during securement of the securing device therewith.

When connecting member 120 is secured in receiver member 130, locking arm 36 can be released by depressing extension 34. This rotates release arm 32 and thus locking arm 36 away from first handle 20, and releasing teeth 42 from engagement with second handle 50. Second handle 50 is then free to pivot from its FIG. 12 position to its FIG. 1 position, drawing reducing member 60 proximally in outer sleeve 100 and allowing arms 80 to open and release receiving member 130.

The anchors and connecting member may be positioned in or along one or more parts of the spine, including the cervical, thoracic, lumbar and/or sacral portions. Although the use of reducing instrument 10 is described in the above context, reducing instrument 10 could be used with a variety of screws, hooks or other fixation implants, or in connection with orthopedic implants in parts of the body other than the spine.

As with other types of orthopedic surgery, an incision is made and access is gained to the surgical site. The approach to the surgical site can be an open approach, i.e. a relatively long incision with retraction of underlying tissue, or can be a minimally invasive approach, i.e. a relatively short incision with implants and tools inserted through retractors or directly through the incision to the surgical site. The reducing instrument disclosed herein can be used in either approach, or with other surgical techniques. It is noted that a relatively narrow distal end of reducing instrument 10 and its pivotal coupling arrangement with the anchor facilitates applications in minimally invasive surgery.

After access to the surgical site has been obtained, anchors such as those including a receiver member 130 are inserted into bone tissue. Such anchors may be pre-fitted with receiver member 130 or other receiver member embodiment, and such anchors typically include a bone engaging portion and a channel for accommodating part of connecting member 120. Such receiver members may also be placed on or over such anchors after engagement of the anchors into bone. A connecting member is inserted into the surgical site, and placed adjacent one or more of the anchors. If not already present, receiver members 130 may be loosely placed on the connecting member prior to insertion of the connecting member to the surgical site. The anchors and connecting member are manipulated so that a part of the connecting member is in or near the each of the anchors.

Reducing instrument 10 is inserted to the surgical site with engaging assembly 16 in an open condition. The surgeon or other operator positions connecting member 120 between arms 80 and about one of the anchors. In the illustrated embodiments, arms 80 are positioned about receiver member 130. Lugs 90 are aligned with detents 138 of receiver member 130, and actuating assembly 12 is manipulated to move arms 80 into engagement with arms 134 of the receiver member 130 with lugs 90 received in detents 138. Reducing instrument 10 can then be pivoted about receiver member 130 to align longitudinal axis 11 with alignment axis 131 between arms 134. Actuating assembly 12 is further manipulated to advance reducing member 60 and position end member 66 in contact with connecting member 120 and position connecting member 120 in recess 68.

With connecting member 120 in recess 68 and arms 134 received in receptacle 94, reducing member 60 is advanced further distally with actuating assembly 12 to seat connecting member 120 in receiver member 130. Teeth 42 of locking arm 36 engage the upper end of receptacle 52 to maintain connecting member 120 in contact with seat 140 of receiver member 130. A set screw is mounted on a driver (not shown) and delivered through bore 78 to engage the internally threaded arms 134 of receiver member 130. The interface between receptacle 94 and receiver member 130 of the anchor maintains bore 78 in alignment with alignment axis 131 extending between arms 134 to, for example, reduce the potential for cross-threading of the set screw with the arms. When connecting member 120 is firmly engaged in receiver member 130, release arm 32 can be moved toward second handle 50, rotating locking arm 36 out of engagement with the upper end of slot 52 and allowing second handle 50 to be pivoted away from first handle 20 about pivot pin 55. This in turn moves reducing member 60 proximally in outer sleeve 100, releasing end member 66 from rails 88 and allowing arms 80 to return toward their biased open position, releasing receiver member 130 from therebetween. Reducing instrument 10 can then be positioned for engagement with the one or more additional anchors if necessary to seat the connecting member therein.

Other arrangements for actuating assembly 12 are contemplated. In the illustrated embodiment, actuating assembly 12 extends laterally from shaft assembly 14 and provides a trigger-like mechanism for operating the actuating system. Other embodiments contemplate other handle arrangements for controlling the depth, angular orientation and rotational orientation of instrument 10. Other suitable examples include T-bars, pistol-grips, hooks, circular finger controls, co-axial shafts, and side-by-side shafts. Shaft assembly 14 has been illustrated with an outer tubular sleeve 100 receiving an inner tubular reducing member 60. Other embodiments contemplate that shaft assembly 14 includes components that are rigid, flexible or a combination of both. Shaft assembly 14 may include one or more tubular elements, rod-like elements, linkages, and elastically deformable members, for example.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An instrument for reducing a connecting member relative to an anchor, comprising:
an actuating assembly;
a shaft assembly extending distally from said actuating assembly, said shaft assembly including a reducing member extending through an outer sleeve, said reducing member being movable distally and proximally relative to said outer sleeve with said actuating assembly; and
an engaging assembly at a distal end of said shaft assembly, said engaging assembly including a pair of arms movable between an open position for receiving the anchor and connecting member therebetween and an engaged position wherein said arms engage opposing sides of the anchor while permitting the instrument to be pivoted about the anchor with the connecting member between the arms, wherein said reducing member includes a distally opening receptacle for receiving the anchor and to align the anchor with said shaft assembly as said reducing member is moved distally toward the anchor to move the connecting member and anchor relative to one another, wherein said pair of arms are pivotally coupled on opposite sides of said outer sleeve, and said reducing member includes a pair of ears extending from opposite sides thereof, said pair of arms extending through respective ones of said pair of ears.

2. The instrument of claim 1, wherein said arms of said engaging assembly each include a lug extending toward the other of said arms, said lugs being pivotally engageable with the anchor.

3. The instrument of claim 2, wherein said lugs each include a cylindrical body extending from said arm, said lugs including a circular cross-section along a length thereof.

4. The instrument of claim 1, wherein each of said pair of arms is pivotally coupled to said outer sleeve.

5. The instrument of claim 1, wherein said actuating assembly includes a first handle pivotally coupled to a second handle.

6. The instrument of claim 5, wherein said first and second handles extend laterally from said shaft assembly.

7. The instrument of claim 5, wherein said actuating assembly includes a locking arm extending between said first and second handles, said locking arm being pivotally coupled to one of said first and second handles and extending through a slot in the other of said first and second handles and being lockingly engageable thereto in said slot.

8. The instrument of claim 7, wherein said actuating assembly further includes a release arm extending from said locking arm along said one of said first and second arm, said release arm being movable to move said locking arm to disengage said locking arm from said slot.

9. The instrument of claim 1, wherein said reducing member includes an end member at a distal end thereof, said end member being positioned distally of a distal end of said outer sleeve.

10. The instrument of claim 9, wherein said end member includes a concavely curved recess for receiving the connecting member when said reducing member is positioned in contact with the connecting member.

11. The instrument of claim 9, wherein said end member defines a receptacle for receiving the anchor as said end member is distally advanced with said actuating assembly toward said anchor.

12. The instrument of claim 9, wherein said end member defines a proximally facing lip extending thereabout, said lip being engageable by a distal end of said outer sleeve when said pair of arms are in said open position.

13. The instrument of claim 1, wherein said outer sleeve includes a pair of opposite wings extending therefrom adjacent a distal end of said outer sleeve, each of said pair of arms being pivotally coupled to a respective one of said pair of wings.

14. The instrument of claim 13, wherein said outer sleeve includes a slot extending therethrough adjacent each of said pair of wings, said pair of arms each including a proximal portion extending through an adjacent one of said slots and contacting said reducing member when said pair of arms are in said open position.

15. The instrument of claim 14, wherein said reducing member includes a proximally tapered portion along said slots, said proximal portions of said pair of arms contacting said proximally tapered portion when in said open position.

16. The instrument of claim 15, wherein said reducing member includes a transition portion extending from a proximal end of said tapered portion to a proximal portion of said reducing member, said proximal portion of said reducing member projecting about said proximal end of said tapered portion.

17. The instrument of claim 16, wherein distal movement of said reducing member moves said transition portion along said proximal portions of said arms until said proximal portion of said reducing member contacts said proximal portions of said arms thereby pivoting said proximal portions of said pair of arms away from one another about said respective wing and moving distal ends of said pair arms toward one another.

18. The instrument of claim 1, wherein said pair of arms each include at least one rail extending proximally from a distal end of said arm, said ears being positioned proximally of said rail of said arm extending therethrough when said arms are in said open position, said ears engaging said rail of said arm extending therethrough when said arms are in said engaged position to maintain said arms in said engaged position.

19. The instrument of claim 1, wherein said pair of arms contact said reducing member in said open position and as said reducing member is moved distally in said outer sleeve and said reducing member moves along proximal portions of said pair of arms to pivot distal ends of said pair of arms toward said engaged position.

20. The instrument of claim 19, wherein when in said engaged position said reducing member engages said pair of arms distally of a pivot location of said pair of arms to maintain said pair of arms in said engaged position.

21. The instrument of claim 19, wherein said pair of arms each include a proximal portion extending through said outer sleeve in contact with said reducing member.

22. An instrument for reducing a connecting member relative to an anchor, comprising:
an actuating assembly;
a shaft assembly extending distally from said actuating assembly, said shaft assembly including a reducing member extending through an outer sleeve, said reducing member being movable distally and proximally relative to said outer sleeve with said actuating assembly; and
an engaging assembly at a distal end of said shaft assembly, said engaging assembly including a pair of arms pivotally coupled to said outer sleeve and movable upon distal advancement of said reducing member relative to said outer sleeve between an open position for receiving the anchor and connecting member therebetween to an engaged position wherein said arms engage opposing sides of the anchor, wherein said reducing member includes a pair of ears extending from opposite sides thereof adjacent a distal end of said reducing member, said pair of arms extending through respective ones of said pair of ears.

23. The instrument of claim 22, wherein said reducing member includes a distally opening receptacle for receiving and aligning the anchor with said shaft assembly as said reducing member is moved distally toward the anchor.

24. The instrument of claim 22, wherein said pair of arms contact said reducing member in said open position and as said reducing member is moved distally in said outer sleeve said reducing member moves along said pair of arms to pivot said pair of arms toward said engaged position.

25. The instrument of claim 22, wherein said reducing member engages said pair of arms in said engaged position to maintain said pair of arms in said engaged position.

26. The instrument of claim 22, wherein said pair of arms each include a proximal portion extending through said outer sleeve in contact with said reducing member in said open position.

27. The instrument of claim 26, wherein said reducing member acts on said pair of arms to move said pair of arms toward said engaged position as said reducing member is advanced distally relative to said outer sleeve.

28. The instrument of claim 22, wherein said arms of said engaging assembly each include a lug extending toward the other of said arms, said lugs pivotally engaging the anchor when said arms are in said engaged position.

29. The instrument of claim 22, wherein said actuating assembly includes a first handle pivotally coupled to a second handle.

30. The instrument of claim 29, wherein said actuating assembly includes a locking arm extending between said first and second handles, said locking arm being pivotally coupled to one of said first and second handles and extending through a slot in the other of said first and second handles and being lockingly engageable thereto in said slot.

31. The instrument of claim 30, wherein said actuating assembly further includes a release arm extending from said locking arm along said one of said first and second arms, said release arm being movable to move said locking arm to disengage said locking arm from said slot.

32. The instrument of claim 22, wherein said reducing member includes an end member at a distal end thereof, said end member being positioned distally of a distal end of said outer sleeve.

33. The instrument of claim 32, wherein said end member includes a concavely curved recess for receiving the connecting member therein when said reducing member is positioned in contact with the connecting member.

34. The instrument of claim 22, wherein said outer sleeve includes a pair of opposite wings extending therefrom adjacent a distal end of said outer sleeve, each of said pair of arms being pivotally coupled to a respective one of said pair of wings.

35. The instrument of claim 34, wherein said outer sleeve includes a slot extending therethrough adjacent each of said pair of wings, said pair of arms each including a proximal portion extending through an adjacent one of said slots and contacting said reducing member when said pair of arms are in said open position.

36. The instrument of claim 35, wherein said reducing member includes a proximally tapered portion along said slots, said proximal portions of said pair of arms contacting said proximally tapered portion when in said open position.

37. The instrument of claim 36, wherein said reducing member includes a transition portion extending from a proximal end of said tapered portion to a proximal portion of said reducing member, said proximal portion of said reducing member projecting about said proximal end of said tapered portion.

38. The instrument of claim 37, wherein distal movement of said reducing member moves said transition portion along said proximal portions of said arms until said proximal portion of said reducing member contacts said proximal portions of said arms thereby pivoting said proximal portions of said pair of arms away from one another about said respective wing and moving distal ends of said pair of arms toward one another to said engaged position.

39. The instrument of claim 22, wherein said pair of arms each include at least one rail extending proximally from a distal end of said arm, each of said ears being positioned proximally of said rail of said arm extending therethrough when said arms are in said open position, each of said ears engaging said rail of said arm extending therethrough when said arms are in said engaged position to maintain said arms in said engaged position.

40. An instrument for reducing a connecting member relative to an anchor, comprising:
  an actuating assembly;
  a shaft assembly extending distally from said actuating assembly, said shaft assembly including a reducing member extending through an outer sleeve, said reducing member being movable distally and proximally relative to said outer sleeve with said actuating assembly; and an engaging assembly at a distal end of said shaft assembly, said engaging assembly including a pair of arms pivotally mounted to said shaft assembly and movable between an open position for receiving the anchor and connecting member therebetween and an engaged position for engaging the anchor therebetween, wherein said reducing member engages said pair of arms in said engaged position to maintain said pair arms in said engaged position, wherein said reducing member includes a pair of ears extending from opposite sides thereof, said pair of arms extending through respective ones of said pair of ears.

41. The instrument of claim 40, wherein said pair of arms are in contact with said reducing member and are moved toward said engaged position by said reducing member upon distal advancement of said reducing member relative to said outer sleeve.

42. The instrument of claim 40, wherein said reducing member includes a distally opening receptacle for receiving the anchor and aligning the anchor with the shaft assembly as said reducing member is moved distally about the anchor.

43. The instrument of claim 40, wherein said pair of arms each include a proximal portion extending through an adjacent slot in said outer sleeve to contact said reducing member in said open position.

44. The instrument of claim 40, wherein said arms of said engaging assembly each include a lug extending toward the other of said arms, said lugs being pivotally engageable to the anchor in said engaged position.

45. The instrument of claim 40, wherein said actuating assembly includes:
  a first handle pivotally coupled to a second handle;
  a locking arm extending between said first and second handles, said locking arm being pivotally coupled to one of said first and second handles and extending through a slot in the other of said first and second handles and being lockingly engageable thereto in said slot.

46. The instrument of claim 45, wherein said actuating assembly further includes a release arm extending from said locking arm along said one of said first and second arm, said release arm being movable to move said locking arm to disengage said locking arm from said slot.

47. The instrument of claim 40, wherein said reducing member includes an end member at a distal end thereof, said end member being positioned distally of a distal end of said outer sleeve.

48. The instrument of claim 47, wherein said end member includes a concavely curved recess for receiving the connecting member therein when said reducing member is positioned in contact with the connecting member.

49. The instrument of claim 40, wherein said outer sleeve includes a pair of opposite wings extending therefrom adjacent a distal end of said outer sleeve, said pair of arms each being pivotally coupled to a respective one of said pair of wings.

50. The instrument of claim 49, wherein said outer sleeve includes a slot extending therethrough adjacent each of said pair of wings, said pair of arms each including a proximal portion extending through an adjacent one of said slots and contacting said reducing member when said pair of arms are in said open position.

51. The instrument of claim 50, wherein said reducing member includes a proximally tapered portion along said slots, said proximal portions of said pair of arms contacting said proximally tapered portion when in said open position.

52. The instrument of claim 51, wherein said reducing member includes a transition portion extending from a proximal end of said tapered portion to a proximal portion of said reducing member, said proximal portion of said reducing member projecting about said proximal end of said tapered portion.

53. The instrument of claim 52, wherein distal movement of said reducing member moves said transition portion along said proximal portions of said arms until said proximal portion of said reducing member contacts said proximal portions of said arms thereby pivoting said proximal portions of said pair of arms away from one another about said respective wing and moving distal ends of said pair of arms toward one another.

54. The instrument of claim 40, wherein said pair of arms each include at least one rail extending proximally from a distal end of said arm, each of said ears being positioned proximally of said rail of said arm extending therethrough when said arms are in said open position, each of said ears engaging said rail of said arm extending therethrough when said arms are in said engaged position to maintain said arms in said engaged position.

* * * * *